United States Patent
Shi et al.

(10) Patent No.: US 11,351,109 B2
(45) Date of Patent: Jun. 7, 2022

(54) COMPOSITION FOR CONDITIONING KERATIN FIBERS

(71) Applicant: L'OREAL, Paris (FR)

(72) Inventors: Li Shi, Shanghai (CN); Haidong Jia, Shanghai (CN)

(73) Assignee: L'OREAL, Paris (FR)

( * ) Notice: Subject to any disclaimer, the term of this patent is extended or adjusted under 35 U.S.C. 154(b) by 722 days.

(21) Appl. No.: 15/531,549

(22) PCT Filed: Dec. 23, 2014

(86) PCT No.: PCT/CN2014/094639
§ 371 (c)(1),
(2) Date: May 30, 2017

(87) PCT Pub. No.: WO2016/101138
PCT Pub. Date: Jun. 30, 2016

(65) Prior Publication Data
US 2017/0333335 A1   Nov. 23, 2017

(51) Int. Cl.
| | | |
|---|---|---|
| *A61Q 5/02* | (2006.01) | |
| *A61Q 5/12* | (2006.01) | |
| *A61K 8/92* | (2006.01) | |
| *A61K 8/33* | (2006.01) | |
| *A61K 8/81* | (2006.01) | |
| *A61K 8/44* | (2006.01) | |
| *A61K 8/46* | (2006.01) | |
| *A61K 8/60* | (2006.01) | |
| *A61K 8/73* | (2006.01) | |

(52) U.S. Cl.
CPC ............. *A61K 8/922* (2013.01); *A61K 8/33* (2013.01); *A61K 8/442* (2013.01); *A61K 8/463* (2013.01); *A61K 8/602* (2013.01); *A61K 8/737* (2013.01); *A61K 8/817* (2013.01); *A61K 8/8141* (2013.01); *A61Q 5/02* (2013.01); *A61Q 5/12* (2013.01); *A61K 2800/34* (2013.01)

(58) Field of Classification Search
None
See application file for complete search history.

(56) References Cited

U.S. PATENT DOCUMENTS

| | | |
|---|---|---|
| 6,432,419 B2 | 8/2002 | Kahre et al. |
| 6,534,455 B1 | 3/2003 | Maurin et al. |
| 8,343,470 B2 * | 1/2013 | Hloucha ............... A61K 8/068 424/401 |
| 2001/0006652 A1 | 7/2001 | Kahre et al. |
| 2002/0187904 A1 | 12/2002 | Perron et al. |
| 2002/0193265 A1 | 12/2002 | Perron et al. |
| 2005/0100523 A1 | 5/2005 | Maubru et al. |
| 2010/0249004 A1 * | 9/2010 | Fack ..................... A61K 8/463 510/124 |
| 2013/0276808 A1 * | 10/2013 | Molenda ................ A61K 8/39 132/202 |

FOREIGN PATENT DOCUMENTS

| | | | |
|---|---|---|---|
| CA | 2 807 386 A1 | 2/2012 | |
| CN | 103068786 A | 4/2013 | |
| DE | 10 2010 062 639 A1 | 10/2011 | |
| EP | 1 232 739 A1 | 8/2002 | |
| EP | 2113240 A1 | 11/2009 | |
| EP | 2191814 A1 * | 6/2010 | ............ A61K 8/19 |
| JP | 8-505875 A | 6/1996 | |
| JP | 2000-512284 A | 9/2000 | |
| JP | 2009-286774 A | 12/2009 | |
| JP | 2013-534218 A | 9/2013 | |
| WO | WO 94/17166 A1 | 8/1994 | |
| WO | WO-9924538 A1 * | 5/1999 | ............ C11D 1/06 |

OTHER PUBLICATIONS

International Search Report and Written Opinion dated Sep. 25, 2015, in PCT/CN2014/094639, filed Dec. 23, 2014.
Japanese Office Action dated Apr. 23, 2018 in Japanese Patent Application No. 2017-533274 (with English translation), 8 pages.
Combined Chinese Office Action and Search Report dated Nov. 26, 2019, in Patent Application No. 201480084473.2, 10 pages (with English Translation of Category of Cited Documents).
Extended European Search Report dated Jun. 29, 2018 in Patent Application No. 14908709.0, 5 pages.

* cited by examiner

*Primary Examiner* — Jyothsna A Venkat
(74) *Attorney, Agent, or Firm* — Oblon, McClelland, Maier & Neustadt, L.L.P.

(57) ABSTRACT

Disclosed is a composition comprising, in an aqueous phase: a) at least one ether of formula (I): R—O—R' in which R and R', which may be identical or different, denotes a linear or branched $C_6$-$C_{25}$ alkyl or alkenyl radical, R and R' being chosen such that the ether is liquid at a temperature of less than or equal to 30° C.; b) at least one surfactant chosen from anionic surfactant, amphoteric or zwitterionic surfactant, or a mixture thereof; c) at least one cationic alkyldiallylamine or dialkyldiallylammonium cyclopolymer; and d) soybean oil.

5 Claims, No Drawings

COMPOSITION FOR CONDITIONING KERATIN FIBERS

FIELD OF THE INVENTION

The present invention relates to hair care cosmetic field, more specifically, it relates to new compositions having improved conditioning properties to the hair after application.

BACKGROUND OF THE INVENTION

It is known to the art to use detergent and conditioning hair care composition, or shampoos, based essentially on surfactants, in particular of the anionic, nonionic, and/or amphoteric type, in combination with conditioning agents.

Surfactants such as anionic surfactants, amphoteric surfactants, or a mixture are commonly known for the ability of removing the various kinds of soil initially present in the hair, and thus possess good washing power. However along with this property, the surfactants may bring to the hair damages due to their aggressive nature of such a cleansing treatment, which leading to the pronounced damage to the hair, such as progressive removal of the lipids or proteins contained in or at the surfactant of the hair.

In order to improve the cosmetic properties of the above detergent composition, and more especially detergent compositions for application to sensitized hair, i.e., hair which is damaged or weakened, in particular through the chemical action of environmental agents and/or of hair treatments such as permanent-waving, dyeing or bleaching, it is known to introduce into these compositions conditioning agents. The main purpose of these conditioning agents is to rectify or limit the undesirable effects induced by the various treatments or types of attach to which the hair fibers are more or less repeatedly subjected to and, of course, they can also improve the cosmetic behavior of natural hair.

The conditioning agents most commonly used to date in shampoos are cationic polymers, silicones and/or silicone derivatives which impart to washed, dry or wet hair a disentangling, softness and a smoothness which are markedly enhanced in comparison to what can be obtained with corresponding cleansing compositions which do not contain them.

Moreover, it is also known to combine more than one conditioning agents in shampoos to obtain even better conditioning effect to the hair, especially to the sensitized hair. Different types of silicones and its derivatives are most commonly combined to achieve this purpose.

On the other hand, efforts had been made to hair care products containing oils such as alkyl ethers, plant oils, mineral oils, for providing to the hair fibers equivalent conditioning effects as those containing silicones as conditioning agent.

It has been found that, in spite of the current progress in the field of shampoos based on a combination of particularly and appropriately selected types of oils other than silicones, and cationic polymers, they are not completely satisfactory, especially in terms of disentangling on damaged hair, for example bleached hair.

Thus there is still a need for new products displaying improved performance in respect to one or more of the cosmetic properties mentioned above.

The present invention is directed towards meeting this need.

BRIEF DESCRIPTION OF THE INVENTION

One aim of the present invention is to obtain a composition, especially for washing and conditioning keratin materials, especially the hair, more particularly the damaged hair such as the bleached hair, which possesses an improved combing ability (disentangling) after application.

The aim of the present invention is achieved by a composition comprising, in an aqueous phase: at least one ether of formula R—O—R', at least one surfactant, at least one cationic alkyldiallylamine or dialkyldiallylammonium cyclopolymer, and soybean oil.

Preferably, the composition of the present invention is silicone-free.

Another aspect of the invention is a process for washing and conditioning keratin fibers, especially the hair, comprising the steps of applying to said fibers the composition of the present invention, and then rinsing with water.

Yet another aspect of the present invention is the use of the composition of the invention for washing and conditioning keratin fibers, especially hair, and more particularly damaged hair like bleached hair.

For the purpose of the invention, the term "damaged hair" refers to hair which are subjected to chemical or physical stress, in particular through the chemical action of environmental agents and/or of hair treatments such as permanent-waving, dyeing or bleaching. Preferably the damaged hair in the present invention refers to the bleached hair.

As used herein, the term "silicone-free" means the composition of the present invention comprising no silicone or comprising silicone in an amount no more than 1% by weight of silicones relative to the total composition. Preferably, the composition may contain no more than 0.5% by weight, more preferably no more than 0.2% by weight, of silicones relative to the total weight of the composition.

In the description, the terms "at least a" or "at least one" are equivalent to "one or more".

Other characteristics and advantages of the invention will emerge more clearly on reading the description and the examples that follow.

DETAILED DESCRIPTION OF THE PRESENT INVENTION

Ether of formula (I) R—O—R'

According to an embodiment, the composition of the present invention comprises at least one ether of formula (I), $$R—O—R' \quad \text{formula (I)}$$

In the formula (I):

R and R', which may be identical or different, denote a linear or branched $C_6$-$C_{25}$ alkyl or alkenyl radical, R and R' being chosen such that the ether is liquid at a temperature of less than or equal to 30° C.

Preferably, the ether of formula (I) is chosen from compounds for which the radicals R and R', which may be identical or different, denote a linear or branched $C_6$-$C_{12}$ alkyl or alkenyl radical. More particularly, according to the present invention, the radicals R and R' are identical alkyl radical.

Amongst ether of formula (I), the preferred dialkyl ether is chosen from di-n-hexyl ether, di-n-heptyl ether, di-n-octyl ether, di-n-nonyl ether, di-n-decyl ether, di-isodecyl ether, di-n-dodecyl ether, di-n-eteradecyl ether, di-n-hexadecyl ether, di-n-oxtadecyl ether, or a mixture thereof.

R and R' preferentially denote a $C_8$ radical.

The dialkyl ethers that may be used according to the invention may be soluble or insoluble in the compositions, but are preferably insoluble.

These compounds may be prepared according to the process described in patent application DE 41 27 230.

Most preferably, a di-n-octyl ether (INCI name: dicaprylyl ether) that may be used in the context of the present invention. Such product is commercially available, for example those sold under the name Cetiol® OE by the company Cognis (BASF), or Rofetan OE by the company Ecogreen Oleochemicals.

The composition according to the invention more particularly has ether content of from 0.01% to 5% by weight, preferably from 0.05% to 3% by weight, more preferably from 0.1% to 1% by weight, relative to the weight of the composition.

Surfactants

The composition according to the invention comprises surfactants. These surfactants are preferably selected from the group consisting of anionic surfactant, amphoteric surfactant, or a mixture thereof.

i) Anionic Surfactant

Anionic surfactant useful in the composition of the invention is understood to mean an amphiphilic compound in which the hydrophobic part carries an anionic hydrophilic group with a cationic counterion which is generally metallic (alkali metal, such as Na or K) or ammonium; the hydrophilic group is thus polar and capable of dissociating to give anions in aqueous solution.

More particularly the anionic part of the anionic surfactant is belonging to the group chosen from: $C(O)OH$, $—C(O)O^-$, $—SO_3H$, $—S(O)_2O^-$, $—OS(O)_2OH$, $—OS(O)_2O^-$, $—P(O)OH_2$, $—P(O)_2O^-$, $—P(O)O_2^-$, $—P(OH)_2$, $=P(O)OH$, $—P(OH)O^-$, $=P(O)O^-$, $=POH$, $=PO^-$, the anionic part comprising a cationic counter anion such as alkali metal such as sodium, or alkaline earth metal such as magnesium, or organic cationic counter anion such as ammonium salts, amine salts, or aminoalcohol salts.

The surfactants may also occur in their acid forms. Mention may be made, as anionic surfactants or surface-active agents, of surfactants or surface-active agents comprising carboxylate, sulfate, sulfonate, sulfoacetate, sulfosuccinate, phosphate, isethionate, sarcosinate, glutamate, lactylate or taurate anionic groups, salts of fatty acids, salts of galactosiduronic acids, salts of ether carboxylic acids surfactants and their mixtures.

More particularly, the anionic surfactants or surface-active agents or agents according to the invention are chosen from:

($C_6$-$C_{30}$)alkyl sulfates, ($C_6$-$C_{30}$)alkyl ether sulfates, ($C_6$-$C_{30}$)alkylamido ether sulfates, alkylaryl polyether sulfates or monoglyceride sulfates; preferably for this type of anionic surfactants, ($C_6$-$C_{30}$)alkyl ether sulfates, alkylaryl polyether sulfates, or a mixture is used.

Mentions may be made of sulfate of ether of lauryl alcohol and alkylene oxide, containing from 1 to 50 alkylene oxide groups.

More preferably, the anionic surfactants is chosen from sulfate of ether of lauryl alcohol and alkylene oxide containing from 1 to 4 alkylene oxide groups, especially ethylene oxide groups. For example, sodium laureth sulfate containing in average 2.2 ethylene oxide groups that are sold by the companie Cognis (BASF) under the name Texapon® AOS 225 UP, Rhodia under the name Rhodapex® esb-70/fla3, and Clariant under the name Genapol® LRO L'O, and sodium laureth sulfate containing in average 1 ethylene oxide group that is sold by the company Zhejiang Zanyu Technology under the name SLES (N1EO).

($C_6$-$C_{30}$)alkyl sulfonates, ($C_6$-$C_{30}$)alkylamidesulfonates, ($C_6$-$C_{30}$)alkylaryl sulfonates, α-olefin sulfonates, paraffin sulfonates;

($C_6$-$C_{30}$)akyl phosphates;

($C_6$-$C_{30}$)alkyl sulfosuccinates, ($C_6$-$C_{30}$)alkyl ether sulfosuccinates or ($C_6$-$C_{30}$)alkylamido sulfosuccinates;

($C_6$-$C_{30}$)alkyl sulfoacetates;

($C_6$-$C_{24}$)acylsarcosinates;

($C_6$-$C_{24}$)acylglutamates;

($C_6$-$C_{30}$)alkylpolyglycoside carboxylic ethers;

($C_6$-$C_{30}$)alkylpolyglycoside sulfosuccinates;

($C_6$-$C_{30}$)alkyl sulfosuccinamates;

($C_6$-$C_{24}$)acyl isethionates, for example sodium lauroyl methyl isethionate, sodium cocoyl isthionate; mentiones may be made of the sodium lauroyl methyl isethionate which is sold under the trade name ISELUX® LQ-CLR-SB by the company Innospec Active Chemicals;

N—[($C_6$-$C_{24}$)acyl] taurates;

salts of fatty acids;

($C_8$-$C_{20}$)acyl lactylates;

salts of ($C_6$-$C_{30}$)alkyl-D-galactosiduronic acids;

salts of ($C_6$-$C_{30}$)alkyl polyoxyalkylenated ether carboxylic acids, of ($C_6$-$C_{30}$)alkylaryl polyoxyalkylenated ether carboxylic acids or of ($C_6$-$C_{30}$)alkylamido polyoxyalkylenated ether carboxylic acids;

and their mixtures.

The alkyl or acyl radicals of these various anionic surfactants preferably comprise from 12 to 20 carbon atoms.

Furthermore, the oxyalkylenated or polyoxyalkylenated anionic surfactants or surface-active agents preferably comprise from 1 to 50 alkylene oxide groups, more preferably from 1 to 4 alkylene oxide groups, in particular ethylene oxide groups.

Advantageously, according to an embodiment, the present invention comprises at least one anionic surfactant chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates, ($C_6$-$C_{24}$)acyl isethionates, or a mixture thereof.

According to an embodiment of the present invention, the anionic surfactant is preferably chosen from sodium laureth sulfate, sodium lauroyl methyl isethionate, sodium cocoyl isthionate, or a mixture thereof.

More preferably the anionic surfactant is sodium laureth sulfate containing ethylene oxide groups, preferably from 1 to 4 ethylene oxide groups.

Advantageously, the content of anionic surfactant(s) represents from 1% to 50% by weight, with respect to the weight of the composition, preferably from 5% to 30% by weight, with respect to the weight of the composition, or 10% to 25% by weight, with respect to the weight of the composition.

ii) Amphoteric or Zwitterionic Surfactant

The surfactants useful in the composition of the invention can be selected from the amphoteric or zwitterionic surfactants.

The amphoteric or zwitterionic surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of ($C_8$-$C_{20}$)alkylbetaines, sulfobetaines, ($C_8$-$C_{20}$ alkyl)amido($C_2$-$C_8$ alkyl) betaines and ($C_8$-$C_{20}$ alkyl)amido($C_2$-$C_8$ alkyl)sulfobetaines.

Among the ($C_8$-$C_{20}$)alkylbetaines, mentions may be made of cocoylbetaine. For example the products sold by the company Rhodia under the tradename Mirataine® BB/FLA.

Among the optionally quaternized secondary or tertiary aliphatic amine derivatives that may be used, mention may also be made of the products of respective structures (A1) and (A2) below:

$$R_a\text{—CON(Z)CH}_2\text{—(CH}_2)_m\text{—N}^+(R_b)(R_c)(CH_2COO^-) \quad (A1)$$

in which:
$R_a$ represents a $C_{10}$-$C_{30}$ alkyl or alkenyl group derived from an acid $R_a$—COOH preferably present in hydrolysed coconut oil, a heptyl group, a nonyl group or an undecyl group,
$R_b$ represents a p-hydroxyethyl group,
$R_c$ represents a carboxymethyl group;
m is equal to 0, 1 or 2,
Z represents a hydrogen atom or a hydroxyethyl or carboxymethyl group;

$$R_{a'}\text{—CON(Z)CH}_2\text{—(CH}_2)_{m'}\text{—N(B)(B')} \quad (A2)$$

in which:
B represents —$CH_2CH_2OX'$, with X' representing —$CH_2$—COOH, $CH_2$—COOZ', —$CH_2CH_2$—COOH, —$CH_2CH_2$—COOZ', or a hydrogen atom,
B' represents —$(CH_2)_z$—Y', with z=1 or 2, and Y' representing —COOH, —COOZ', —$CH_2$—CHOH—$SO_3H$ or —$CH_2$—CHOH—$SO_3Z'$,
m' is equal to 0, 1 or 2,
Z represents a hydrogen atom or a hydroxyethyl or carboxymethyl group,
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}$-$C_{30}$ alkyl or alkenyl group of an acid $R_{a'}$COOH preferably present in hydrolysed linseed oil or coconut oil, an alkyl group, in particular a $C_{17}$ alkyl group, and its iso form, or an unsaturated $C_{17}$ group.

The compounds corresponding to formula (A1) are preferred.

Among the compounds corresponding to formula (A1), mentions may be made of cocamidopropyl betaine, for example the product sold under the tradename Dehyton PK 45 by Cognis (BASF).

Use may also be made of the compounds of formula (A3):

$$R_{a''}\text{—NH—CH(Y'')—(CH}_2)n\text{-C(O)—NH—(CH}_2)n'\text{—N}(R_d)(R_e) \quad (A3)$$

in which:
$R_{a''}$ represents a $C_{10}$-$C_{30}$ alkyl or alkenyl group of an acid $R_{a''}$—C(O)OH preferably present in hydrolysed linseed oil or coconut oil;
Y'' represents the group —C(O)OH, —C(O)OZ'', —$CH_2$—CH(OH)—$SO_3H$ or the group —$CH_2$—CH(OH)—$SO_3$—Z'', with Z'' representing a cationic counterion resulting from an alkali metal or alkaline-earth metal, such as sodium, an ammonium ion or an ion resulting from an organic amine;
$R_d$ and $R_e$ represent, independently of each other, a $C_1$-$C_4$ alkyl or hydroxyalkyl radical; and
n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name Chimexane HB.

Preferably, the amphoteric surfactants are chosen from ($C_8$-$C_{20}$)alkylbetaines, ($C_8$-$C_{20}$)alkylamido($C_1$-$C_6$)alkylbetaines, and mixtures thereof.

More preferably, the amphoteric or zwitterionic surfactant is chosen from cocamidopropyl betaine, cocoylbetaine, or a mixture thereof.

According to one specific embodiment of the present invention, the amphoteric surfactant ii) mentioned above is cocoylbetaine.

According to a preferred embodiment, the surfactant is present in the composition of the present invention ranging from 1% to 50% by weight, preferably from 5% to 40% by weight, more preferably from 10% to 30% by weight, relative to the total weight of the composition.

Preferably, the composition of the present invention comprises, in addition to the surfactant(s) described above, surfactants chosen from nonionic surfactants, cationic surfactants, or mixtures thereof.

Cationic Alkyldiallylamine or Dialkyldiallylammonium Cyclopolymer

The composition according to the present invention comprises at least one cationic alkyldiallylamine or dialkyldiallylammonium cyclopolymer.

Said cationic cyclopolymer is a homopolymer or copolymer contains, as main constituent of the chain, units corresponding to formula (IV) or (V):

$$-\left(\begin{matrix}H_2\\C\end{matrix}\right)_d\overset{(R^{32})}{C}\overset{(CH_2)_e}{\diagdown}C(R_{32})\overset{H_2}{-}C- \quad (IV)$$
$$\begin{matrix}H_2C & & CH_2\\ & \diagdown N^+ \diagup & \\ & R_{30}\ R_{31}\ Y^- & \end{matrix}$$

$$-\left(\begin{matrix}H_2\\C\end{matrix}\right)_d\overset{(R^{32})}{C}\overset{(CH_2)_e}{\diagdown}C(R_{32})\overset{H_2}{-}C- \quad (V)$$
$$\begin{matrix}H_2C & & CH_2\\ & \diagdown N \diagup & \\ & | & \\ & R_{30} & \end{matrix}$$

in which formula d and e are equal to 0 or 1, the sum d+e being equal to 1; $R_{32}$ denotes a hydrogen atom or a methyl radical; $R_{30}$ and $R_{31}$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; $R_{30}$ and $R_{31}$ can also denote, together with the nitrogen atom to which they are attached, a heterocyclic group such as piperidyl or morpholinyl; $R_{30}$ and $R_{31}$, independently of each other, preferably denote a $C_1$-$C_4$ alkyl group; $Y^-$ is an organic or mineral anion such as bromide, chloride, acetate, borate, citrate, tartrate, bisulfate, bisulfite, sulfate or phosphate.

These polymers are described in particular in FR 2 080 759 and FR 2 190 406.

The cationic cyclopolymer of the present invention is a water soluble polymer having a charge density greater than 4 meq/g, preferably greater than 5 meq/g. The charge density of the water soluble cationic cyclopolymer may be measured by the colloid titration method using, for example, potassium polyvinylsulfate as a titration solution.

Among the polymers defined above, mention may be made more particularly of the dimethyldiallylammonium chloride homopolymer sold under the name "Merquat 100" by the company Nalco (and its homologues of low weight-average molecular mass) and the copolymers of diallyldimethylammonium chloride and of acrylamide, sold under the name Merquat 550.

According to a preferred embodiment, the cationic alkyldiallylamine or dialkyldiallylammonium cyclopolymer is present in the composition of the present invention, ranging from 0.01% to 3% by weight, preferably from 0.05% to 2% by weight, more preferably 0.1% to 1.5% by weight, relative to the total weight of the composition.

Soybean Oil

The composition according to the present invention comprises soybean oil.

As an example of soybean oils, mention may be made of the product sold by the company Huileries De Lapalisse under the tradename HUILE DE SOJA RAFFINEE IP, or those sold by the company Zor under the name Refined CT Soybean oil, or those sold by the company Cargill under the name Non-GMO refined soybean oil.

According to a preferred embodiment, the soybean oil is present in the composition ranging from 0.01% to 3% by weight, preferably 0.1% to 1% by weight, more preferably from 0.2% to 0.5% by weight, relative to the total weight of the composition.

According to a preferred embodiment, the composition of the present invention comprises, in an aqueous phase:
A) at least one ether of formula (I)

$$R\text{---}O\text{---}R' \qquad \text{formula (I)}$$

in which
R and R' are identical to each other, and denote $C_6$-$C_{12}$ alkyl or alkenyl radicals;
B) at least one surfactant chosen from ($C_6$-$C_{30}$)alkyl sulfates, ($C_8$-$C_{20}$) alkylbetains, ($C_8$-$C_{20}$)amido($C_2$-$C_8$ alkyl) betaines, or a mixture thereof;
C) at least one polydiallyl dimethyl ammonium chloride homopolymer; and
D) soybean oil.

According to yet another preferred embodiment, the composition of the present invention comprises, in an aqueous phase, by weight relative to the total weight of the composition:
A1) from 0.01% to 5% by weight of at least one ether of formula (I)

$$R\text{---}O\text{---}R' \qquad \text{formula (I)}$$

in which:
R and R' are identical to each other, and denote $C_6$-$C_{12}$ alkyl or alkenyl radicals;
B1) from 10% to 30% by weight of a mixture of ($C_6$-$C_{30}$) alkyl sulfates and ($C_8$-$C_{20}$) alkylbetains;
C1) from 0.01% to 3% by weight of at least one polydiallyl dimethyl ammonium chloride homopolymer; and
D1) from 0.01% to 3% by weight of soybean oil.

The compositions according to the invention may naturally contain, in addition, all the standard adjuvants encountered in the field of shampoos, such as, for example, perfumes, preservatives, sequestering agents, thickeners, hydrating agents, anti-dandruff or antiseborrhoeic agents, vitamins, sunscreen agents, suspending agents and the like.

The composition according to the invention may take the form of liquid, creams or gel.

Another aspect of the invention is a process for washing and conditioning keratin fibers, especially the hair, comprising the steps of applying to said fibers the composition of the invention, and then rinsing with water after an optional period of exposure.

Yet another aspect of the present invention is the use of the above composition of the invention for washing and conditioning keratin fibers, especially hair.

Non limiting examples illustrating the invention are given.

EXAMPLES

Four hair shampoos were prepared, one according to the invention (Invention A) and three comparative (Comparative B, C and D):

| Ingredient (Chemical or INCI name) | Invention A (% by weight, by active ingredient) | Comparative B (% by weight, by active ingredient) | Comparative C (% by weight, by active ingredient) | Comparative D (% by weight, by active ingredient) | Control |
|---|---|---|---|---|---|
| Sodium laureth sulfate (2EO) (Texapon ® AOS 225 UP from Cognis (BASF)) | 14.00 | 14.00 | 14.00 | 14.00 | 9 |
| Cocoylbetaine (Mirataine ® BB/FLA from Rhodia) | 5.00 | 5.00 | 5.00 | 5.00 | 0 |
| Polyquaternium-6 (Merquat 100 from Nalco) | 0.40 | 0.40 | 0 | 0 | 0 |
| Dicarprylyl Ether (Cetiol ® OE from Cognis (BASF)) | 0.50 | 0.50 | 0.50 | 0.50 | 0 |
| Soybean oil (Non-GMO refined soybean oil from Cargill) | 0.25 | 0 | 0.25 | 0.25 | 0 |
| Olive oil | 0 | 0.25 | 0 | 0 | 0 |
| Guar hydroxypropyl trimonium chloride | 0 | 0 | 0.40 | 0 | 0 |
| Polyquaternium-10 (UCARE POLYMER JR 400 LT from Dow Chemical) | 0 | 0 | 0 | 0.40 | 0 |

-continued

| Ingredient (Chemical or INCI name) | Invention A (% by weight, by active ingredient) | Comparative B (% by weight, by active ingredient) | Comparative C (% by weight, by active ingredient) | Comparative D (% by weight, by active ingredient) | Control |
|---|---|---|---|---|---|
| Preservative | 1.00 | 1.00 | 1.00 | 1.00 | 0 |
| Carbomer (Carbopol ® 980 from Lubrizol) | 0.40 | 0.40 | 0.40 | 0.40 | 0 |
| WATER | Qs to 100 | Qs to 100 | Qs to 100 | Qs to 100 | Qs to 100 |
| pH | 5-5.5 | 5-5.5 | 5-5.5 | 5-5.5 | / |

Control was used for washing bleached Chinese hair sold by the company IHIP USA, before the evaluation.

In Comparative B, the soybean oil of the invention was replaced by olive oil; In Comparative C, the polyquaternium-6 of the invention was replaced by guar hydroxypropyl trimonium chloride, in Comparative D, the polyquaternium-6 was replaced by Polyquaternium-10.

The invention A, Comparative B, C and D were prepared according to the conventional methods for preparing shampoo formulations.

The reduction of combing force on the bleached hair of the Invention A, Comparative B, C, and D formulated above were evaluated.

Dry Combing after Rinsing 4 g of the examples of Invention A and Comparative B, C and D samples were applied on 10 g of bleached Chinese hair sold by the company IHIP USA, respectively. The examples were then left on the hair for 1 minute. Then the hair was rinsed by warm water for 10 seconds, and left to dry over night at room temperature. After 3 times repeated application using the process described herein, the combing force between the hair stress and a comb was measured by the device named Diastron MTT175, sold by JIN HONGFAN.

The reduction of combing force was measured based on the following formula:

Reduction of combing force (%)=[combing force of control(9% of sodium laureth sulfate)−combing force of example)/combing force of 9% sodium laureth sulfate]×100%.

It is considered that the product is acceptable when the reduction of combing force is greater than or equal to 10%.

| | Reduction of dry combing force (%) | | | |
|---|---|---|---|---|
| Attribute | Invention A | Comparative B | Comparative C | Comparative D |
| Bleached Chinese hair | 15% | 6% | −4% | 9% |

Result: the dry combing force of the bleached hair using Invention A has been reduced significantly, comparing to that of the Comparative B, C and D.

Panel Test

Shampooing was performed by applying approximately 4 g of the Invention A, Comparative B, C and D on 10 g middle damaged hair swatch available on the market sold by the company IHIP USA, respectively. The invention A, Comparative B, C and D were then left on the swatch for 1 minute. Then the swatch was rinsed by warm water for 10 seconds, and blown dry and cooled to 25° C.

A panel of 6 experts evaluated the detangling of the wet hair, the ease of shaping, the softness, smoothness, and suppleness of the hair. The performances of each were sorted by level 0 to 5, whereas 0 represents bad performance, and 5 represents excellent performance.

It is considered that the product is acceptable when the score is greater than or equal to 3.

The results of the evaluation were listed:

| | Performance | | | |
|---|---|---|---|---|
| Property | Invention A | Comparative B | Comparative C | Comparative D |
| Detangling of wet hair | 4.2 | 3.9 | 2.6 | 2.8 |
| Wet-smoothness | 4.1 | 4 | 2.8 | 3.4 |
| Wet-suppleness | 4.2 | 3.6 | 3.9 | 4.1 |
| Dry combing | 4.2 | 3.8 | 3.4 | 3.3 |
| Dry-smoothness | 4.2 | 3.3 | 3.4 | 3.8 |
| Dry-Suppleness | 4 | 3.2 | 3.2 | 3.7 |

Result: based on the evaluation made by the panels, Invention A has an improvement in all of these properties with comparison to the Comparative B, C and D.

What is claimed is:

1. A shampoo composition comprising, in an aqueous phase:
   a) 0.1% to 1% by weight of dicaprylyl ether;
   b) from 10% to 25% by weight of sodium laureth sulfate and from 5% to 10% by weight of cocoyl betaine;
   c) from 0.1% to 1.5% by weight of polydiallyl dimethyl ammonium chloride homopolymer; and
   d) from 0.1% to 1% by weight of soybean oil,
   all weights being based on the weight of the composition.

2. The composition of claim 1, wherein the composition is free of silicone.

3. The composition according to claim 1, wherein the soybean oil is present in the composition in an amount ranging from 0.2% to 0.5% by weight, relative to the total weight of the composition.

4. A process for washing and conditioning hair, comprising: applying to said hair the composition of claim 1; and then rinsing with water.

5. The process according to claim 4, wherein the hair is damaged hair.

* * * * *